US 12,310,579 B2

(12) United States Patent
Sauer

(10) Patent No.: US 12,310,579 B2
(45) Date of Patent: May 27, 2025

(54) DEVICE FOR SUTURE TENSIONING AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 680 days.

(21) Appl. No.: 17/617,356

(22) PCT Filed: Jun. 10, 2020

(86) PCT No.: PCT/US2020/036947
§ 371 (c)(1),
(2) Date: Dec. 8, 2021

(87) PCT Pub. No.: WO2020/251986
PCT Pub. Date: Dec. 17, 2020

(65) Prior Publication Data
US 2022/0225978 A1    Jul. 21, 2022

Related U.S. Application Data

(60) Provisional application No. 62/859,446, filed on Jun. 10, 2019.

(51) Int. Cl.
*A61B 17/04*        (2006.01)
*A61B 17/00*        (2006.01)
*A61B 90/00*        (2016.01)

(52) U.S. Cl.
CPC ...... *A61B 17/0482* (2013.01); *A61B 17/0469* (2013.01); *A61B 2017/00424* (2013.01);
(Continued)

(58) Field of Classification Search
CPC ............ A61B 17/0482; A61B 17/0469; A61B 17/0487; A61B 17/0483;
(Continued)

(56) References Cited

U.S. PATENT DOCUMENTS 5,364,407 A  *  11/1994  Poll .................... A61B 17/0487
                                                     606/232
2007/0156027 A1 *  7/2007  Hu ......................... A61B 90/57
                                                     600/231
(Continued)

FOREIGN PATENT DOCUMENTS

EP    2628451    1/2016
EP    3278741    2/2018
(Continued)

OTHER PUBLICATIONS

International Preliminary Report on Patentability for PCT/US2020/036947, International filing date Jun. 10, 2020, LSI Solutions, Inc., 6 pages.
(Continued)

*Primary Examiner* — Brigid K Byrd
(74) *Attorney, Agent, or Firm* — Michael E. Coyne

(57) ABSTRACT

A device for suture management and tensioning is disclosed. The device for suture tensioning may include a housing having multiple suture channels, a cleat array, several indicator biasing elements, and an actuator movable between an unlocked position, a tensioned position, and a locked position. The cleat array in the device for suture tensioning may also include at least one first cleat movable relative to the housing and colinear with a second cleat fixedly attached to the housing. The device for suture tensioning may also include an indicator biasing element which is colinear with each cleat pair.

13 Claims, 12 Drawing Sheets

(52) U.S. Cl.
CPC ............... *A61B 2017/0496* (2013.01); *A61B 2090/0807* (2016.02)

(58) Field of Classification Search
CPC .... A61B 2017/0496; A61B 2017/0488; A61B 2017/00424; A61B 17/0485; A61B 17/0467; A61B 2090/0807
See application file for complete search history.

(56) References Cited

U.S. PATENT DOCUMENTS

| | | | |
|---|---|---|---|
| 2008/0228165 A1 | 9/2008 | Spence et al. | |
| 2010/0106194 A1 | 4/2010 | Bonutti et al. | |
| 2012/0226310 A1* | 9/2012 | Frankland | A61B 17/0487 606/232 |
| 2013/0158600 A1 | 6/2013 | Conklin et al. | |
| 2013/0218206 A1* | 8/2013 | Gadlage | A61B 17/0487 606/232 |
| 2014/0163615 A1* | 6/2014 | Gadlage | A61B 17/0487 606/232 |
| 2014/0352594 A1 | 12/2014 | Kruger | |
| 2015/0245901 A1 | 9/2015 | Dougherty et al. | |

FOREIGN PATENT DOCUMENTS

| | | |
|---|---|---|
| JP | 2009-502233 | 1/2009 |
| WO | 2015095133 | 6/2015 |
| WO | 2016007973 | 1/2016 |
| WO | 2019055433 | 3/2019 |

OTHER PUBLICATIONS

Extended European Search Report for EP20823023, dated Jan. 5, 2023, 12 pages.

* cited by examiner

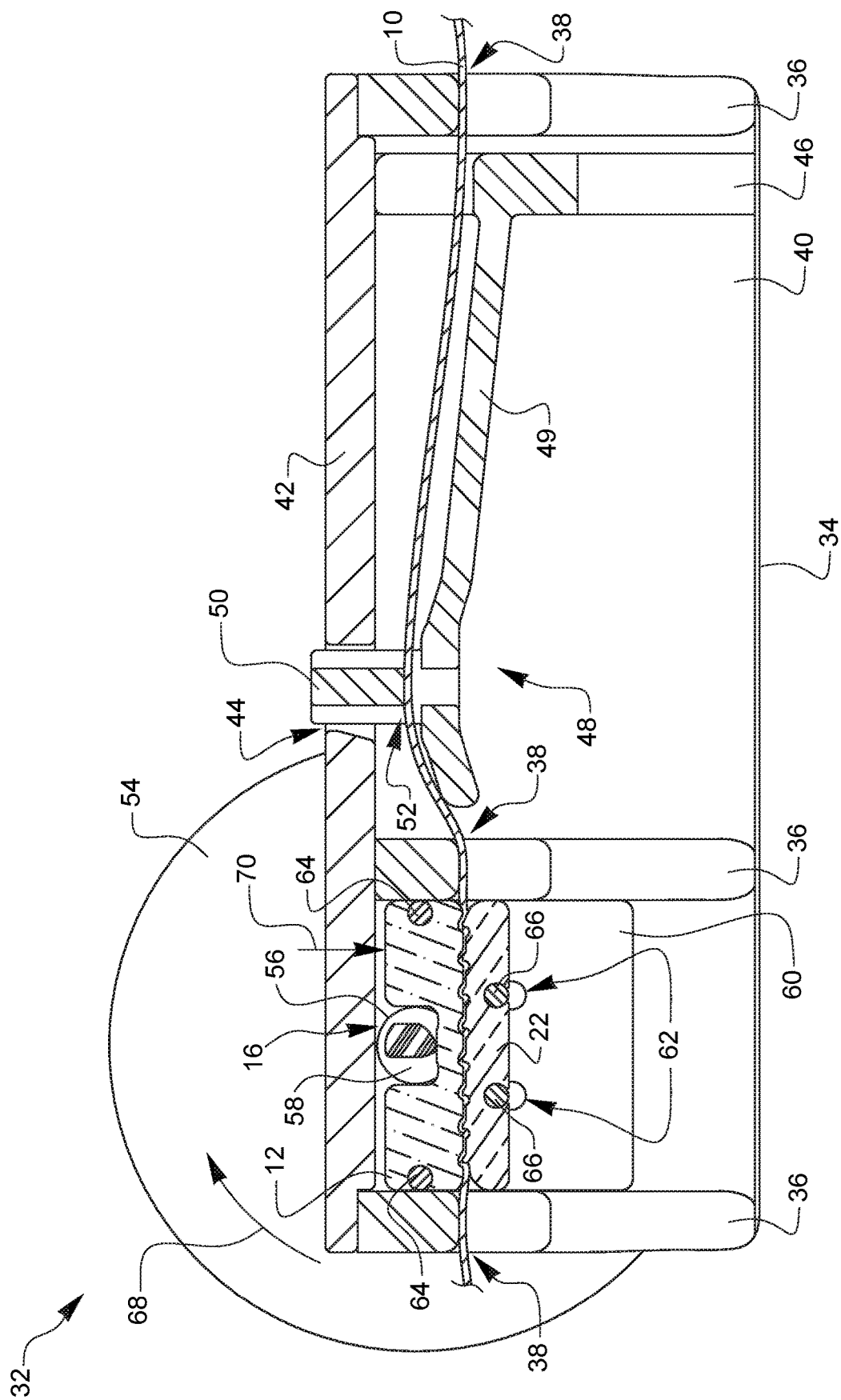

DEVICE FOR SUTURE TENSIONING AND METHODS THEREOF

REFERENCE TO RELATED APPLICATIONS

This application is a national stage application, filed under 35 U.S.C. § 371, of International Patent Application No. PCT/US20/36947, filed on Jun. 10, 2020, which claims priority to U.S. Provisional Patent Application No. 62/859,446, filed Jun. 10, 2019, the contents of each of which is hereby incorporated by reference in its entirety.

FIELD

The claimed invention relates to surgical devices, and more specifically to devices used in the management and tensioning of suture for minimally invasive surgical procedures.

BACKGROUND

Modern advances in minimally invasive cardiac surgery have enabled surgeons to perform surgical procedures which extend patient lives and improve patient quality of life while reducing post-operative pain, hospital stays, and post-operative limitations. Among such minimally invasive procedures, tricuspid valve repair is one of the more challenging procedures. In addition to the specialized medical knowledge and surgical skills needed to complete such a procedure, surgeons and their medical staff must also be very adept at suture management. It is desirable to have improved apparatuses which help surgical staff with suture management and maintaining appropriate suture tension. It would also be desirable to have improved apparatuses for suture management and tensioning which provide additional security and visual feedback to surgical staff during modern minimally invasive surgical procedures.

SUMMARY

A device for tensioning suture is disclosed. The device also includes a housing; a first cleat having a first gripping surface, the first cleat movably connected to the housing; a second cleat which is colinear with the first cleat and having a second gripping surface, the second cleat connected to the housing, where the second gripping surface is opposing the first gripping surface; an indicator biasing element connected to the housing and colinear with the first cleat and the second cleat; and an actuator connected to the housing and in contact with the first cleat.

The device for tensioning suture also includes a housing having a plurality of suture channels; a cleat array which may include: a first cleat array portion movably connected to the housing, the first cleat array portion may include a plurality of first cleats, each first cleat may include a first gripping surface, and a plurality of spacer blocks interposed between each first cleat; and a second cleat array portion fixedly connected to the housing, the second cleat array portion may include a plurality of second cleats, each second cleat may include a second gripping surface, where each second cleat is colinear with each first cleat, and a plurality of spacer blocks interposed between each second cleat. The device for tensioning suture also includes a plurality of indicator biasing elements, each indicator biasing element connected to the housing and colinear with the first cleat and the second cleat and each indicator biasing element may include a suture channel; and an actuator connected to the housing and in contact with the first cleat array portion where the actuator is movable between an unlocked position, a tensioned position, and a locked position.

BRIEF DESCRIPTION OF DRAWINGS

FIGS. 2A-2D are partial cross-sectional views of a suture tensioning device during operation.

Figure 1A:
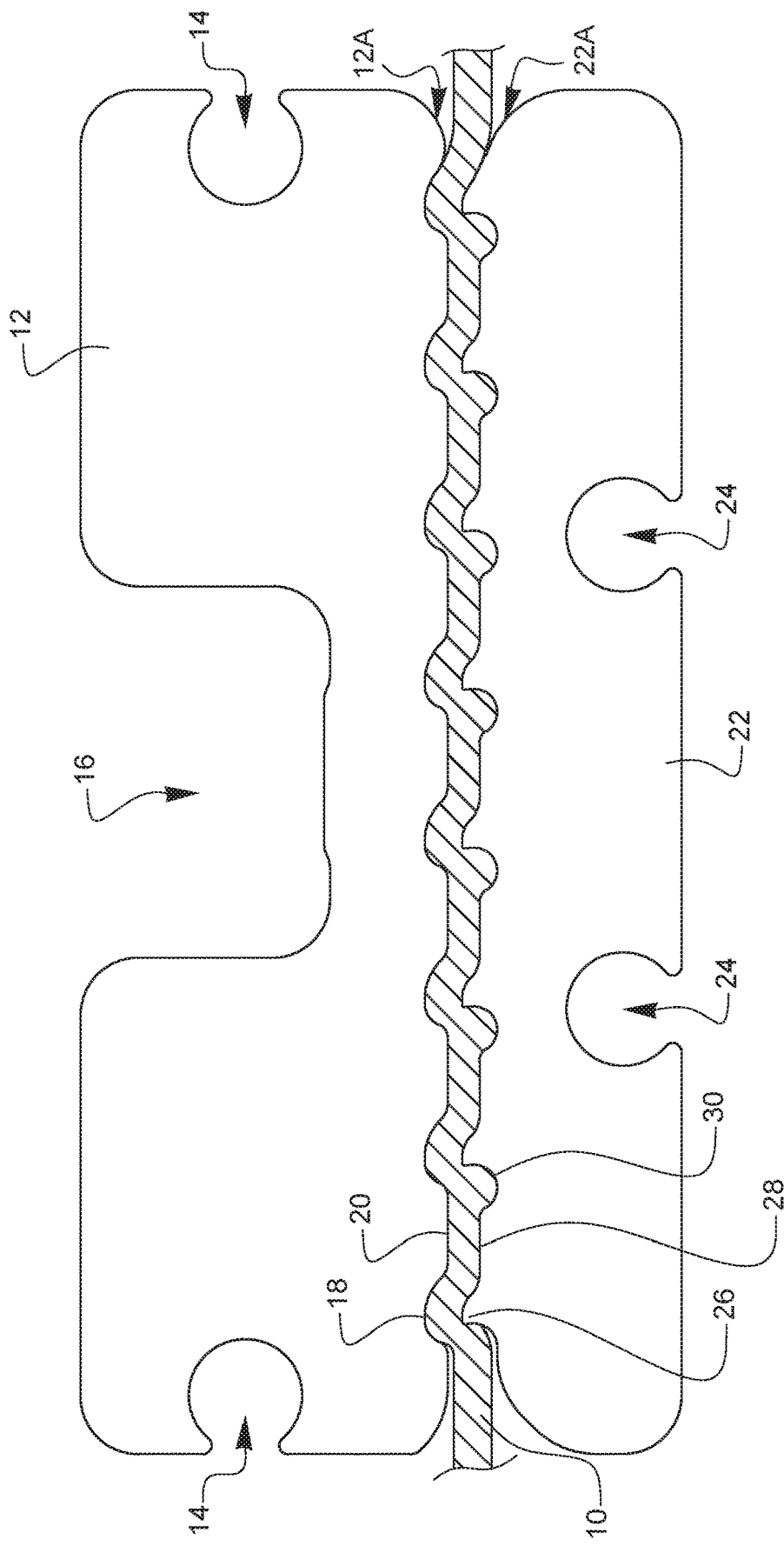
FIG. 1A is a partial cross-sectional view of a suture tensioning device element of a suture tensioning device.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1A is a partial cross-sectional view of a suture tensioning device element of a suture tensioning device. The suture tensioning device element of FIG. 1A is constructed of a first or top cleat 12 and a second or bottom cleat 22. The top cleat 12 has two top cleat holes 14 configured to fasten or hole the top cleat 12 to an external structure or assembly, and a top cleat cam recess 16 configured to accept a cam (not shown here but will be discussed later in further detail). The suture facing gripping surface 12A of the top cleat 12 also has several alternating surface recesses 18 and flat spots 20 configured to hold suture 10 with sufficient force when opposing or held in opposition to the bottom cleat 22. The bottom cleat 22 has two bottom cleat holes 24 configured to fasten the bottom cleat 22 to an external structure or assembly. The suture facing gripping surface 22A of the bottom cleat 22 also has several alternating protrusions or surface teeth 26, flat spots 28, and surface recesses 30, configured to hold suture 10 with sufficient force when opposing or held in opposition to the top cleat 12. The top cleat 12 and the bottom cleat 22 are colinear with one another and are arranged such that they lie within the same line or linear arrangement. The asymmetric teeth on the bottom cleat 22 are oriented in an opposing direction relative to the direction that the suture would be tensioned during operation of a suture tensioning device having a cleat pair such as the one depicted herein. The top cleat 12 or bottom cleat 22 may have alternate arrangements of protrusions, surface recesses 18 and flat spots 20, such as alternate numbers of surface recesses 18 and flat spots 20, surface recesses 18 and flat spots 20 arranged in a pattern other than alternating, or composed of similar features having various symmetrical or asymmetrical sizes and shapes, including, but not limited to saw tooth, square, rounded, ramped, triangular, or inversions or combinations thereof. The top cleat may or may not have all the aforementioned features, and the second cleat may or may not have all of the aforementioned features. Asymmetric teeth may be oriented in the same direction as tensioned suture, or in an opposing direction to the direction of the tensioned suture in alternate embodiments. The aforementioned shapes and features may be protruding or recessed from a plane line formed by the suture facing surface and may be composed of one or more than one of the aforementioned shapes or characteristics. The first cleat or top cleat 12 and the second cleat or bottom cleat 22 are constructed of plates that may be made of metal, plastic, or other rigid materials capable of holding sufficient holding force on a suture in such a configuration. It should be understood that the term "suture," as used herein, is intended to cover any thread, cable, wire, filament, strand, line, yarn, gut, or similar structure, whether natural and/or synthetic, in monofilament, composite filament, or multifilament form (whether braided, woven, twisted, or otherwise held together), as well as equivalents, substitutions, combinations, and pluralities thereof for such materials and structures.

Figure 1B:
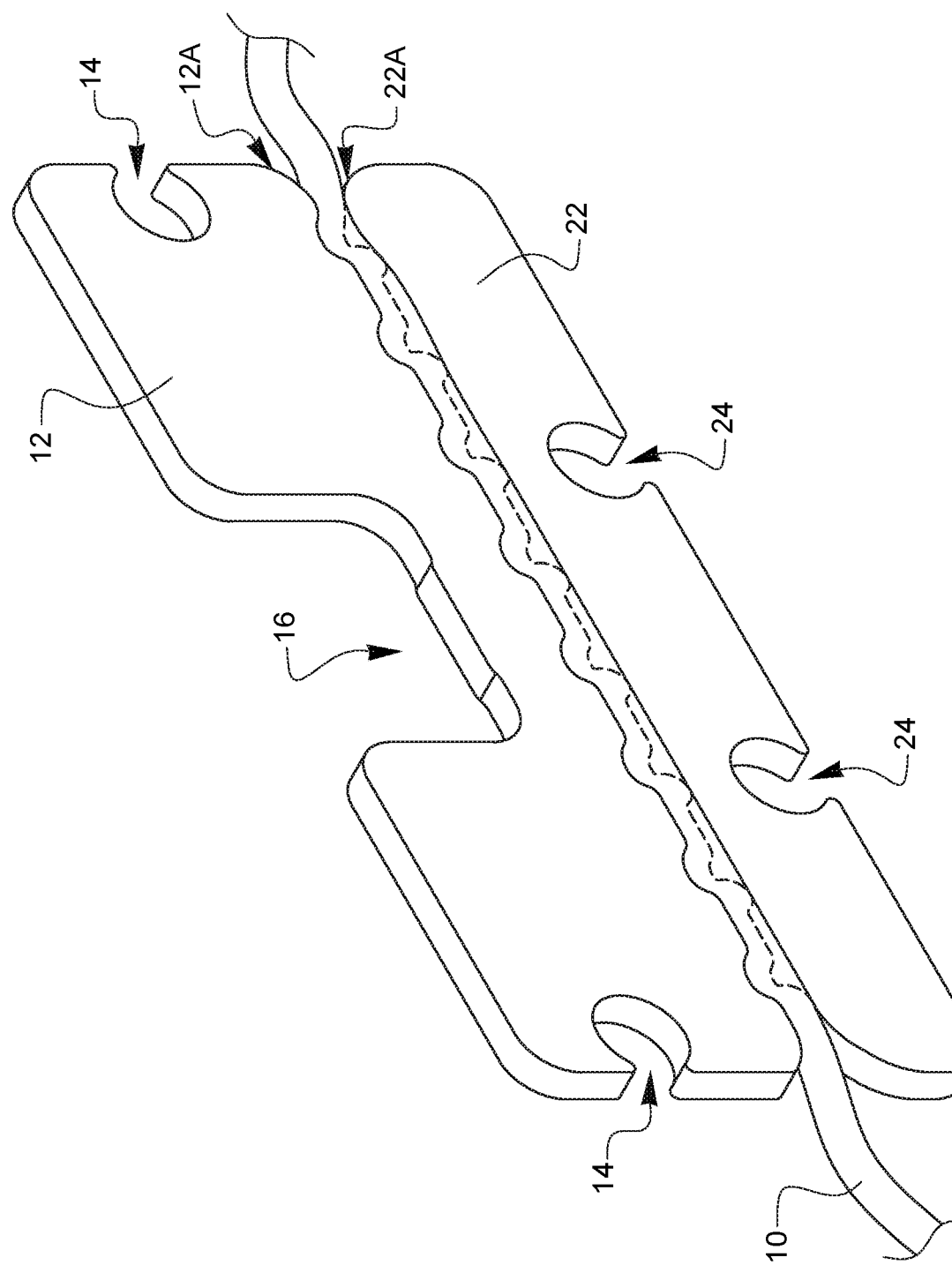
FIG. 1B is a top-left-front perspective view of the suture tensioning device element of FIG. 1A.

It should be noted that sufficient force refers to a minimum threshold level of force required to hold and tension suture between two opposing gripping surfaces configured in a locked position. Sufficient force may be dictated by a specific surgical procedural consideration, suture material property, or overall device configuration. Alternate suture materials or configurations may result in different actual values in terms of sufficient force required for holding and tensioning suture during minimally invasive surgical procedures. As an example, certain surgical procedures may require a holding force or tensioning force of at least 1 kg on a suture in order to pull one or more sutures simultaneously held in a tensioning device. The configuration or arrangement of a cleat pair may be modified in order to deliver this amount of holding force or tension. FIG. 1B is a top-left-front perspective view of the suture tensioning device element of FIG. 1A. Similar to the view in FIG. 1A, the suture 10 is shown held between the top cleat 12 and the bottom cleat 22.

Figure 2A:
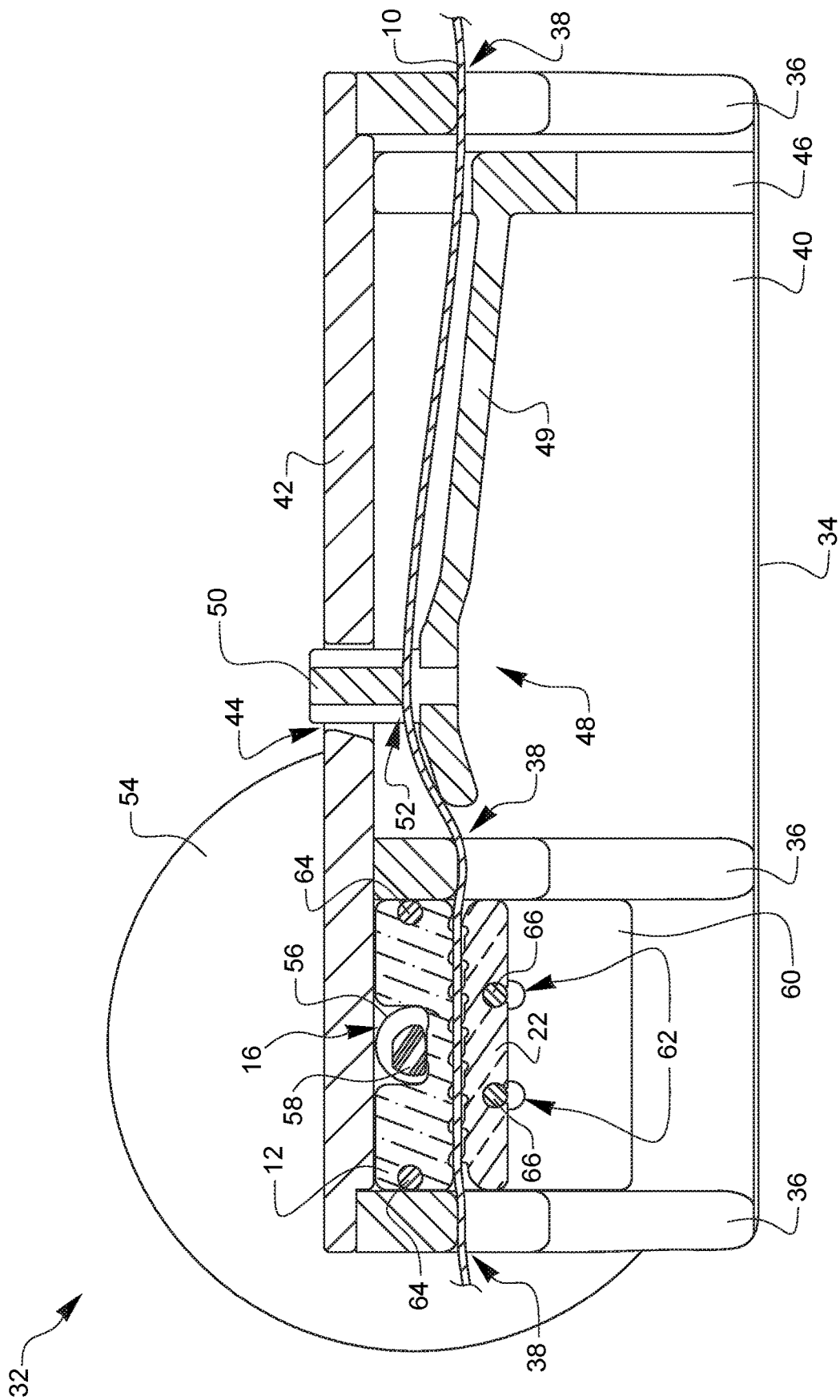

FIGS. 2A-2D are partial cross-sectional views of a suture tensioning device during operation. FIG. 2A illustrates a suture tensioning device 32 having a tensioning device body 34, several support walls 36, each of the support walls 36 having a suture channel 38 configured to pass suture 10 therethrough and a side wall 40. The suture tensioning device 32 also has a device cover 42 which may or may not be removable. The device cover 42 has an opening 44 configured to allow visualization of the top portion 50 of an indicator biasing element 48 by the user. The indicator biasing element 48 also has a beam 49. The indicator biasing element 48 is connected to the device body 34 via an element support 46. The indicator biasing element 48 also has a biasing element suture channel 52 passing therethrough, which is configured to receive suture. The location of the biasing element suture channel 52 on the indicator biasing element 48 is such that when suture 10 passing through the channel 52 is under tension, the beam 49 of the indicator biasing element 48 is configured to flex, and the top portion 50 is lowered relative to its position shown in FIG. 2A. Thus, the indicator biasing element 48 is colinear with both the top cleat 12 and the bottom cleat 22. The pair of the top cleat 12 and the bottom cleat 22 may also be referred to as a cleat pair.

The suture tensioning device 32 also has an actuator 54 coupled to an actuator mount 56. A cam 58 is coupled to the actuator mount 56 which rotates when the actuator 54 is rotated. As the cam 58 is rotated through various positions, the cam 58 contacts the top cleat cam recess 16 of the top cleat 12, moving the top cleat 12 into various vertical positions in relation to the bottom cleat 22. Positioned between two support walls 36 is an alignment side plate 60 having two alignment side plate pin guides 62 attached to the top cleat 12 via two top cleat pins 64. The two top cleat pins also attach a corresponding alignment side plate (not shown in this view) to an opposing side of the top cleat 12. The top cleat 12 and its associated structure are movable within the device body 34 of the suture tensioning device 32. The bottom cleat 22 is fixedly attached to the device body 34 via two bottom cleat pins 66. The two bottom cleat pins 66 are passed through the alignment side plate pin guides 62 in the alignment side plate 60 for the purpose of vertically aligning the top cleat 12 and the bottom cleat 22 while the top cleat 12 is moved through its various positions. While the motion of the actuator brings the top cleat 12 closer to the bottom cleat 22, the first cleat 12 and the second cleat 22 are not in contact and the suture passage through the various suture channels 38, 52 in the suture tensioning device 32 is not restricted when the actuator 54 is in the unlocked position shown in FIG. 2A.

FIG. 2B illustrates a partial cross-section of the suture tensioning device 32 with the actuator 54 moved into a partial tensioned position. When the actuator 54 is rotated in movement direction 68 the cam 58 also moves into a position where a different point on the radius of the cam 58 is in contact with the top cleat cam recess 16. This position of the movement direction 68 coordinates with a partially locked position. In this partially locked position, the suture is only under a partial amount of the total force that can be delivered by the suture tensioning device 32. In this position of the top cleat 12 relative to the bottom cleat 22, the suture is held within the suture tensioning device 32 and can be moved through the device, with some resistance. In this partial locked or tensioned position, the suture 10 can travel through the various suture channels 38, 52 in the suture tensioning device 32. FIG. 2B illustrates the suture tensioning device 32 in a partially locked position, where the first cleat 12 and the second cleat 22 are in partial contact and suture passage through the various suture channels 38, 52 in the suture tensioning device 32 is partially restricted. If the device 32 or suture 10 are moved relative to one another, there will be some drag or friction on the movement due to the partially tensioned state of the top cleat 12 relative to the bottom cleat 22.

Figure 2C:
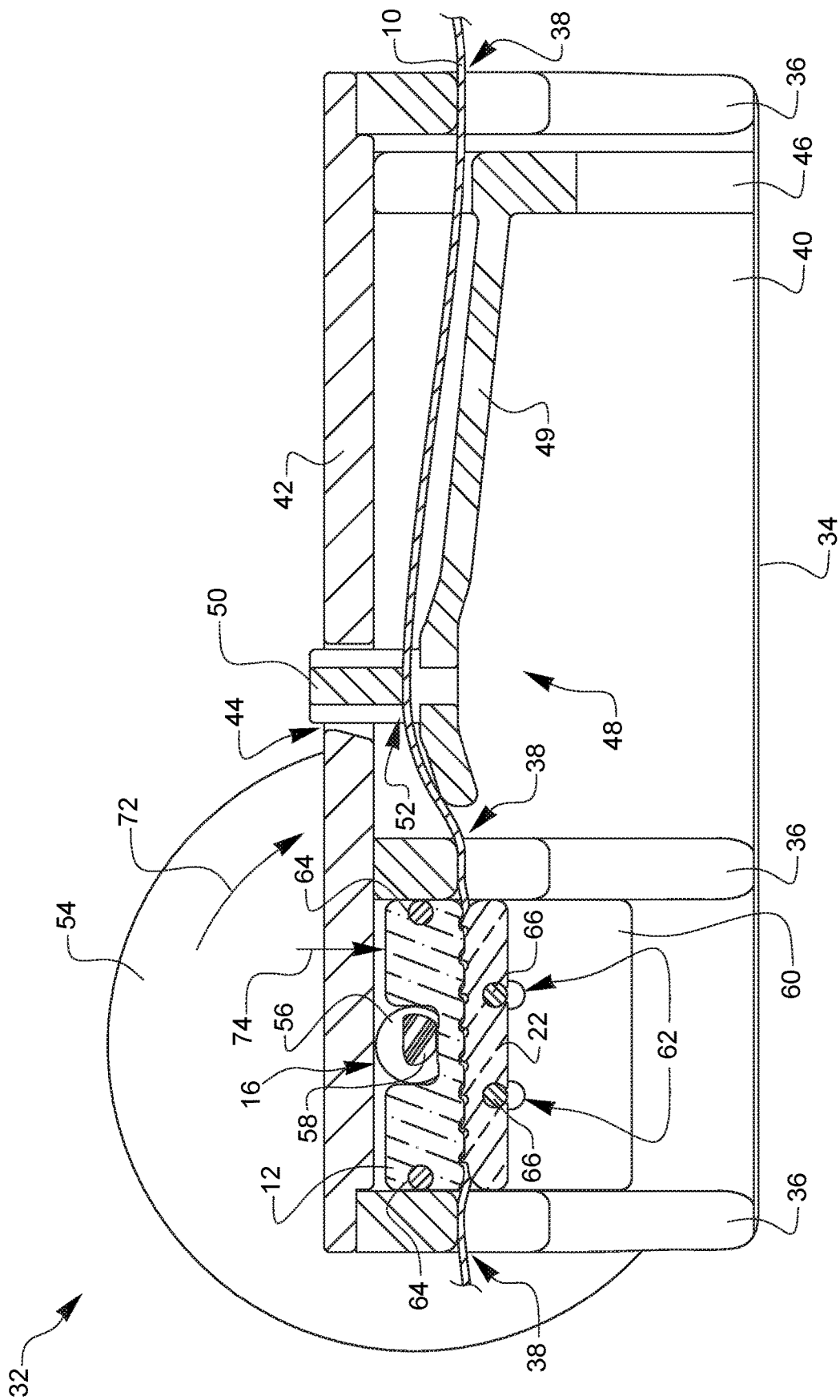

FIG. 2C illustrates a partial cross-section of the suture tensioning device 32 with the actuator 54 moved into a fully locked position. When the actuator 54 is rotated in movement direction 72 the cam 58 also moves into a position where a different point on the radius of the cam 58 is in contact with the top cleat cam recess 16. This position of the movement direction 72 coordinates with a fully locked position. In this fully locked position, the suture 10 is under the maximum amount of the total force that can be delivered by the suture tensioning device 32. FIG. 2C illustrates the suture tensioning device 32 in a fully locked or locked position or configuration, such that the first cleat 12 and the second cleat 22 are in full contact and suture 10 passage through the various suture channels 38, 52 in the suture tensioning device 32 is fully restricted when the actuator 54 is in the locked position.

Figure 2D:
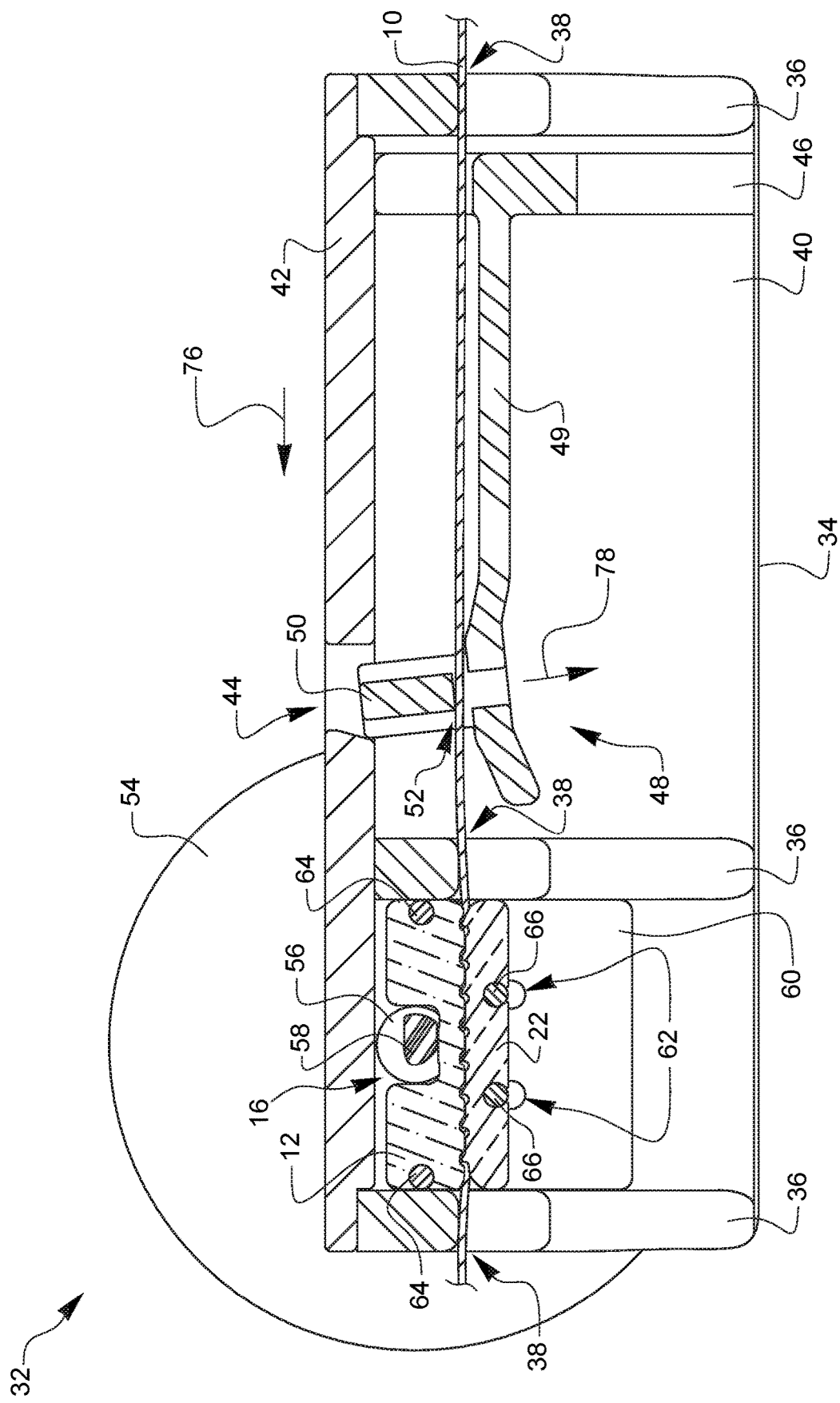

FIG. 2D illustrates a partial cross-section of the suture tensioning device 32 with the actuator 54 in a fully locked position. Upon positioning and locking a suture 10 within the various suture channels 38, 52 in the suture tensioning device 32, visual confirmation of appropriate suture tension may be desirable. It is also desirable in some minimally invasive surgical procedures to tighten suture once it has been secured in a suture tensioning device 32 such as the one shown and described herein. As the suture tensioning device 32 is pulled in a direction 76, the suture is pulled taut, and is held firmly between the locked first cleat 12 and bottom cleat 22. Since the suture 10 is threaded through the suture channel 38 and the indicator biasing element suture channel 52, the suture 10 is moved from a loose configuration to a straight configuration when tightened, as shown in FIG. 2D. The indicator biasing element 48 thus moves downward in direction 78, moving the top portion 50 of the indicator biasing element 48 out of the opening 44 of the device cover 42. This provides a visual indication to the operator that appropriate tension on the suture has been achieved within the suture tensioning device 32. This visual effect is reversible and as tension on the device is relaxed, the indicator biasing element 48 will return to its original configuration and the top portion 50 of the indicator biasing element 48 returns to its original position in the opening 44 of the device cover 42. The indicator biasing element 48 is designed and configured such that a threshold required level of tensioning force is on suture when locked. This amount of force needed for visual confirmation may be modified by utilizing alternate shapes materials or biasing element shapes. This may provide alternate levels of tensioning or visualization methods to indicate the appropriate tension on the suture has been achieved by locking the device. While the movement of the indicator biasing element 48 is shown as a means of tension visualization, other means known to those skilled in the art may also be used, such as color, letter, numeral, symbol, sound, or lighting effect.

Figure 3B:
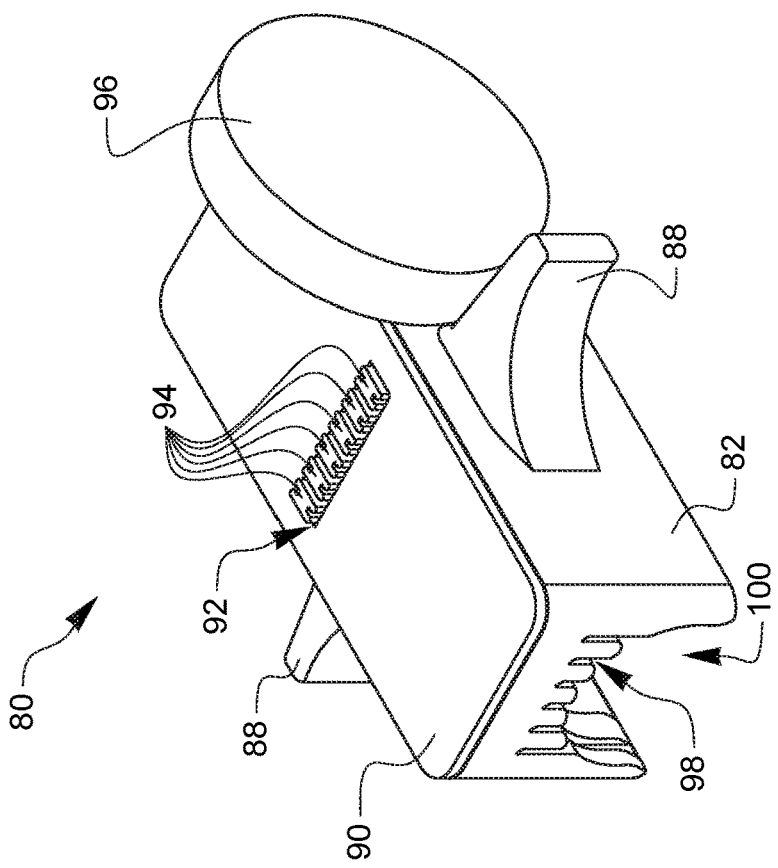
FIGS. 3A and 3B are top-left-front and top-left-rear perspective views, respectively, of an embodiment of a suture tensioning device capable of tensioning six sutures.
Figure 3A:
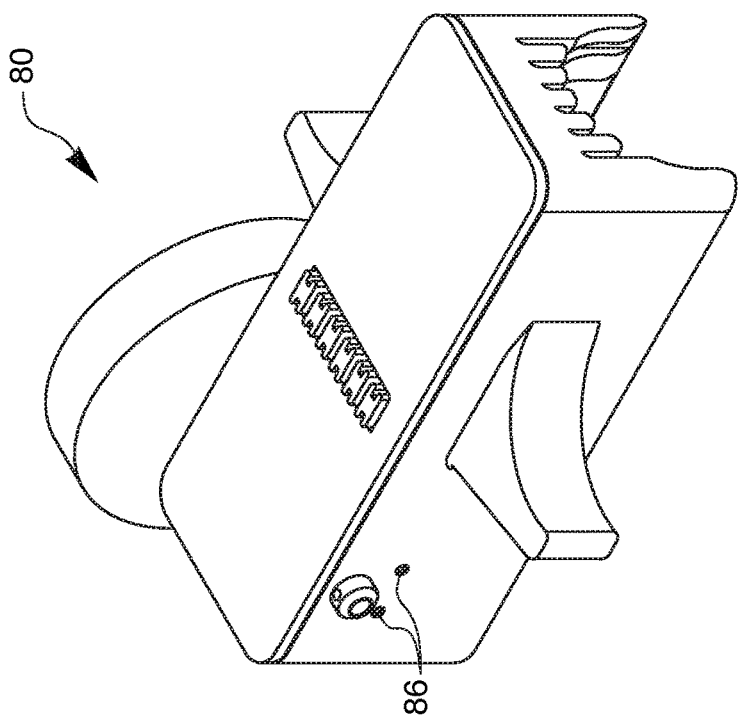

FIGS. 3A and 3B are top-left-front and top-left-rear perspective views, respectively, of an embodiment of a suture tensioning device capable of tensioning six sutures. A suture tensioning device 80 is illustrated having a body 82, the body having two ergonomic gripping features 88, an actuator 96 and a shaft recess 100. The ergonomic gripping features 88 are configured such that they provide a comfortable hand position for holding and pulling multiple locked and tensioned sutures during a minimally invasive surgical procedure. The actuator 96 rotates a cam that engages in a cam recess in a top cleat such as those described in regard to FIGS. 2A-2D. The shaft recess 100 is configured such that it and locks onto the shaft of a crimping instrument. Above the shaft recess 100 are several external suture channels 98 for the purpose of directing and organizing multiple sutures. The suture tensioning device 80 has a cover 90 with a cover opening 92 whereby six indicator tops 94 are visible therethrough. This embodiment of a suture tensioning device 80 has the capacity to lock, tension and provide visual indication related to six separate sutures used in a minimally invasive surgical procedure. FIG. 3A further illustrates the location of several top cleat pin locations 84, not shown in this view, and bottom cleat pin locations 86, showing the relative locations of the various cleat pairs within the suture tensioning device 80.

Figure 4:
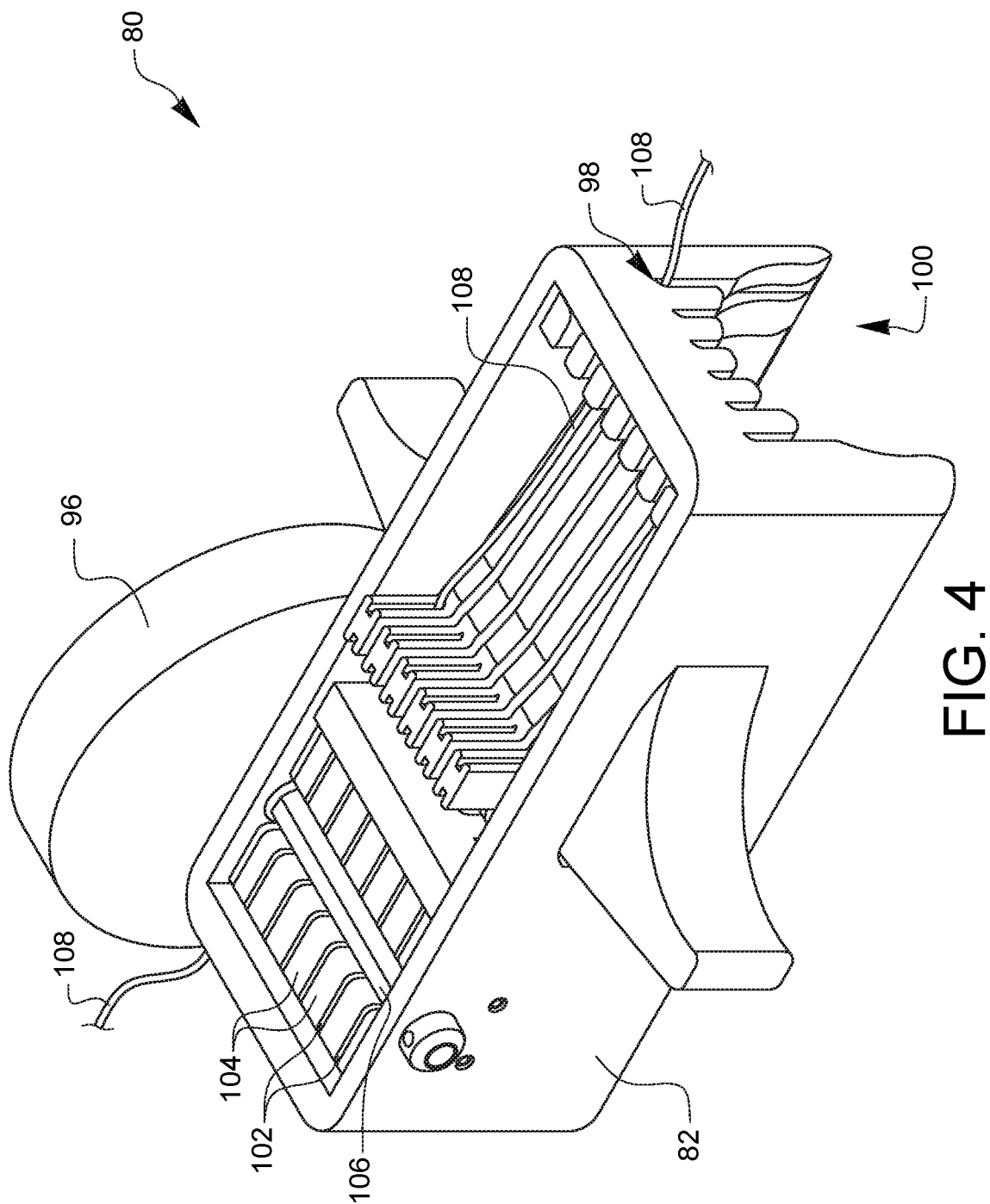
FIG. 4 is a top-left-front perspective view of the suture tensioning device of FIG. 3A with the cover removed.

FIG. 4 is a top-left-front perspective view of the suture tensioning device of FIG. 3A with the cover removed. The suture tensioning device 80 is shown with a suture 108 threaded through the device 80 and exiting through one of the suture channels 98. With the cover removed, several top cleats 102 are visible, with multiple spacers 104 placed in between the top cleats 102. The cam 106 attached to the actuator 96 is shown resting in a cam recess formed by the top cleats 102 and spacers 104. These spacer blocks 104 are interposed between each of the top cleats 102.

Figure 5:
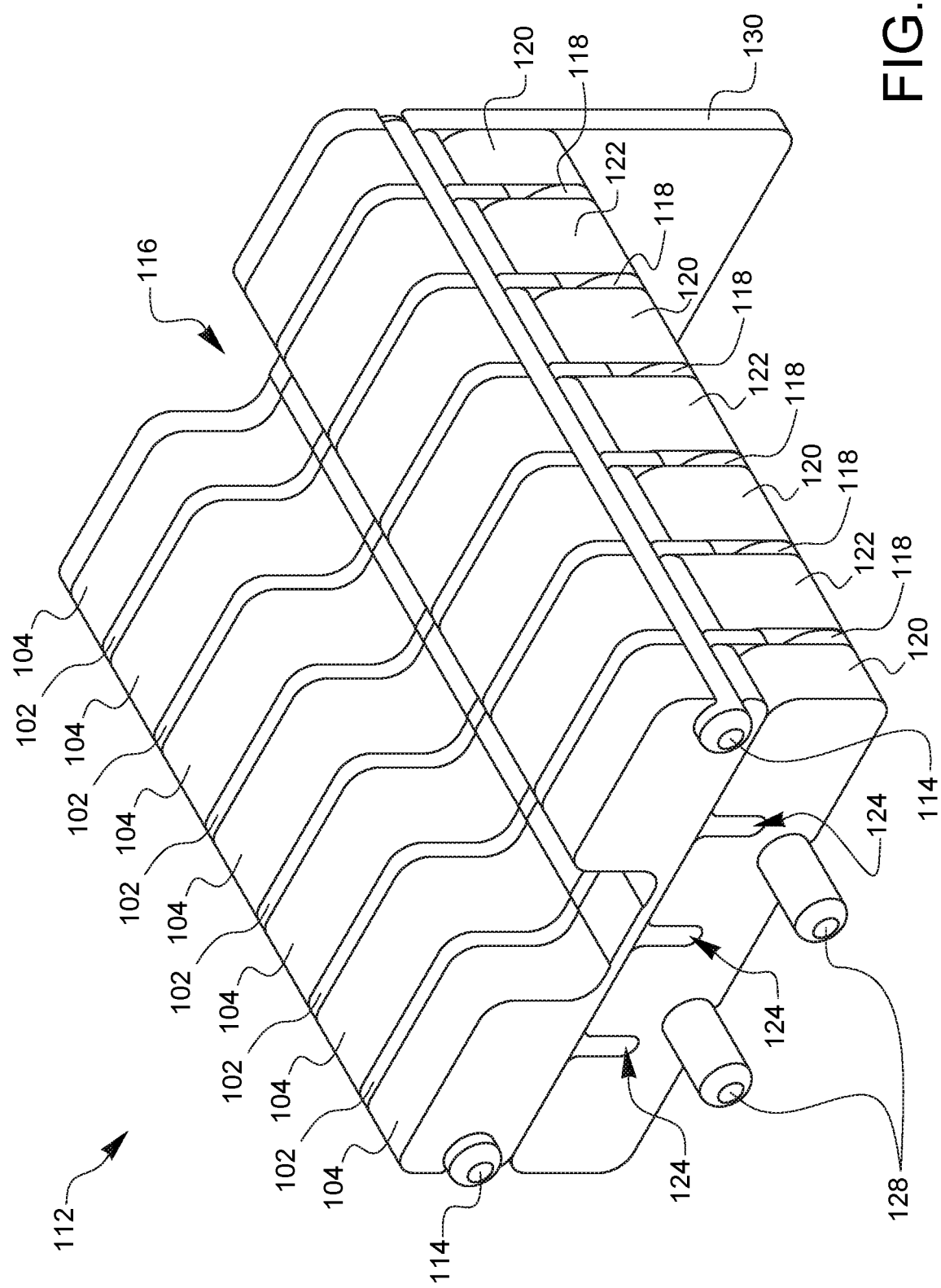
FIG. 5 is a top-left-front perspective view of a cleat array of the suture tensioning device of FIGS. 3A and 3B.

FIG. 5 is a top-left-front perspective view of a cleat array of the suture tensioning device of FIGS. 3A and 3B. A cleat array 112 is shown in FIG. 5, which is constructed from several top cleats 102 and top cleat spacers 104, interposed along the length of the top cleat array portion. The top cleat array portion is held together by two top cleat pins 114. The individual components and the combined structure formed by the top cleats 102 and top cleat spacers 104 form an array cam recess 116 which receives a cam as described in previous embodiments herein. The cleat array 112 also contains several bottom cleats 118 interposed between several first bottom cleat spacers 120 and several second bottom cleat spacers 122. The first bottom cleat spacer 120 has several relief recesses 124, forming a bottom cleat array portion. The second bottom cleat spacers 122 also have several relief recesses 126 which are not shown in this view. The purpose of these relief recesses 124, 126 are to allow for suture to expand from out of the space between the top cleat 102 and the bottom cleat 118 when in the locked position. In some suture materials, in particular, suture made from expanded polytetrafluoroethylene (ePTFE), the suture may expand in an outward direction when under compression forces such as those created by the locking mechanism of the top and bottom cleats. Suture of such a design or material may break under tension if spatial allowance for expansion of suture under pressure is not made. These spacers or spacer blocks may have alternate arrangements, shapes or configurations of relief recesses known to those skilled in the art. The bottom array portion is held together by two bottom cleat pins 128. The top portion and bottom portion of the array are held within a side alignment plate 130. A corresponding side alignment plate 130 would be part of the cleat array 112, but this one is not shown for purposes of visibility. The two alignment plates receive the top cleat pins 114 and bottom cleat pins 128 and align the top cleats 102 with the bottom cleats 118. While this embodiment shows the cleat array being constructed of several pieces attached together to form the cleat array 112, other embodiments may have a top portion or a bottom portion or both composed of a single piece while having some or all of the features and structure of the illustrated embodiment. These array pieces may be molded, printed, or machined out of a plastic material, or machined, printed, or cast of a metal or metal alloy material. Other materials or methods of constructing cleat arrays as described will be known to those skilled in the art.

Figure 6A:
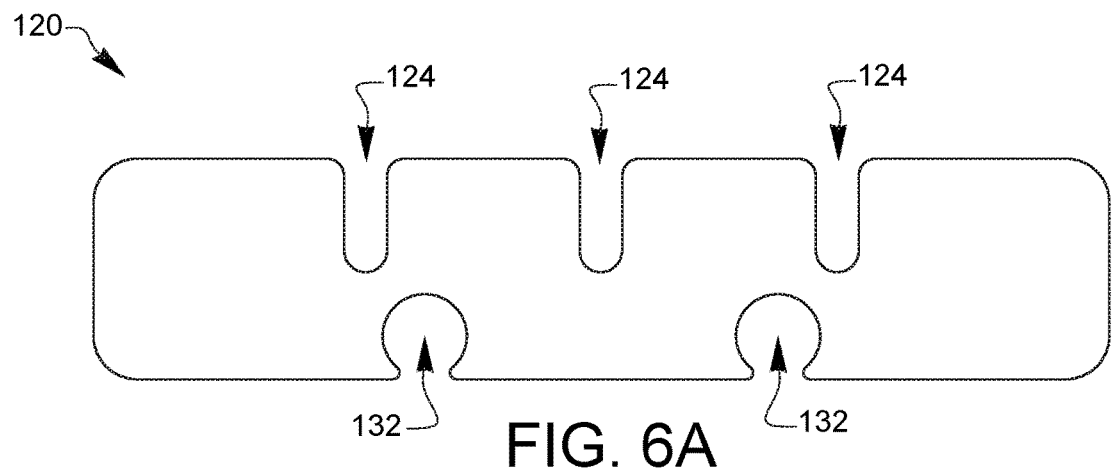
FIGS. 6A-6C are side views of different spacer elements of the cleat array of FIG. 5.
Figure 6B:
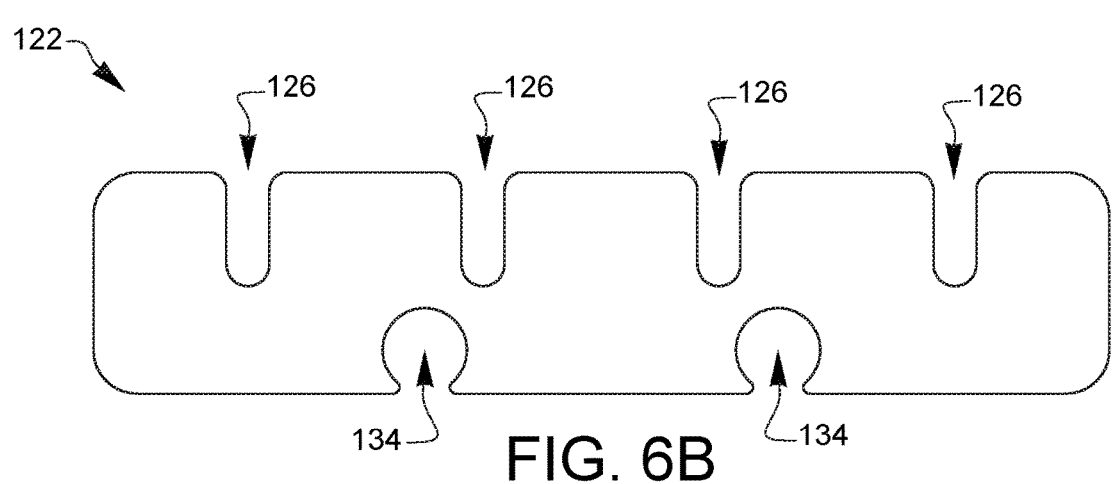
Figure 6C:
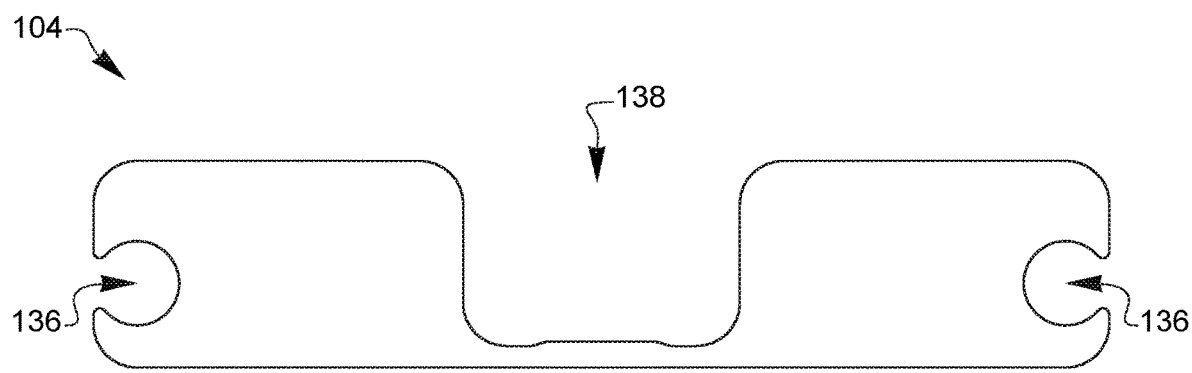

FIGS. 6A-6C are side views of different spacer elements of the cleat array of FIG. 5. FIG. 6A is a side view of a first bottom cleat spacer 120 demonstrating the location of the pin holes 132 and spacer recesses 124 defined by the first bottom cleat spacer 120. FIG. 6B is a side view of a second bottom cleat spacer 122 demonstrating the location of the pin holes 134 and spacer recesses 126 defined by the second bottom cleat spacer 122. FIG. 6C is a side view of a top cleat spacer 104 demonstrating the location of the pin holes 136 and cam recess 138 defined by the top cleat spacer 104.

Figure 7:
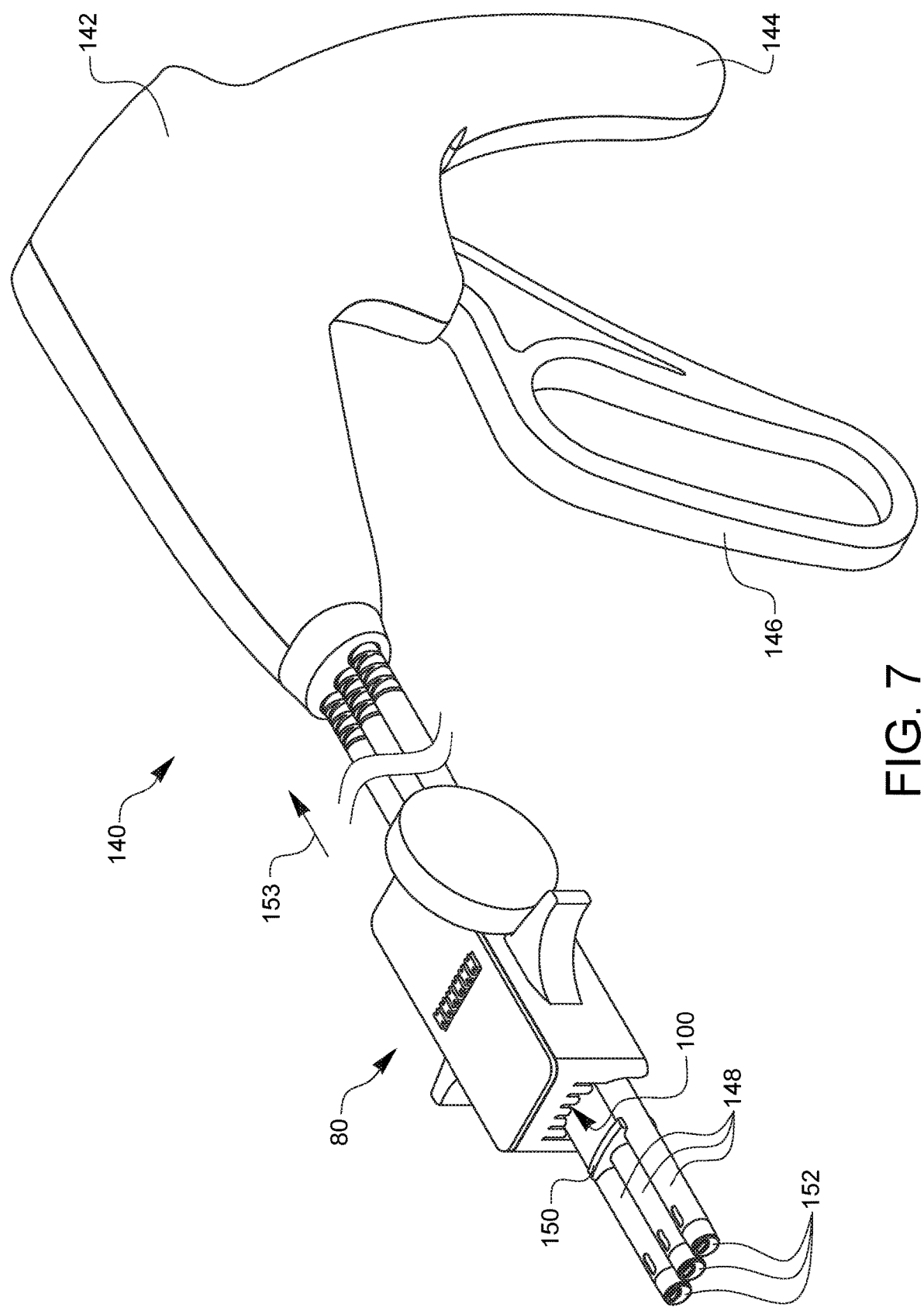
FIG. 7 is a top-left-rear perspective view of an embodiment of a crimping instrument, with the suture tensioning device of FIG. 3A loaded onto the shaft.

FIG. 7 is a top-left-rear perspective view of an embodiment of a crimping instrument, with the suture tensioning device of FIG. 3A loaded onto the shaft. An embodiment of a crimping instrument 140, having three shafts 148, a shaft support 150, and three crimping ends 152, can fasten three mechanical knots simultaneously. The crimping instrument 140 has a housing 142 defining a handle 144. The instrument 140 has an actuation lever 146 which simultaneously crimps the mechanical fasteners and cuts sutures when actuated. The suture tensioning device 80 is placed onto the instrument over the shafts 148. The suture tensioning device 80 is slidably engaged along the shafts 148 by placing the shaft recess 100 over the shafts 148 and can be pulled in a direction towards 153 the operator for the purpose of tensioning suture threaded through one or more mechanical fasteners.

Figure 8:
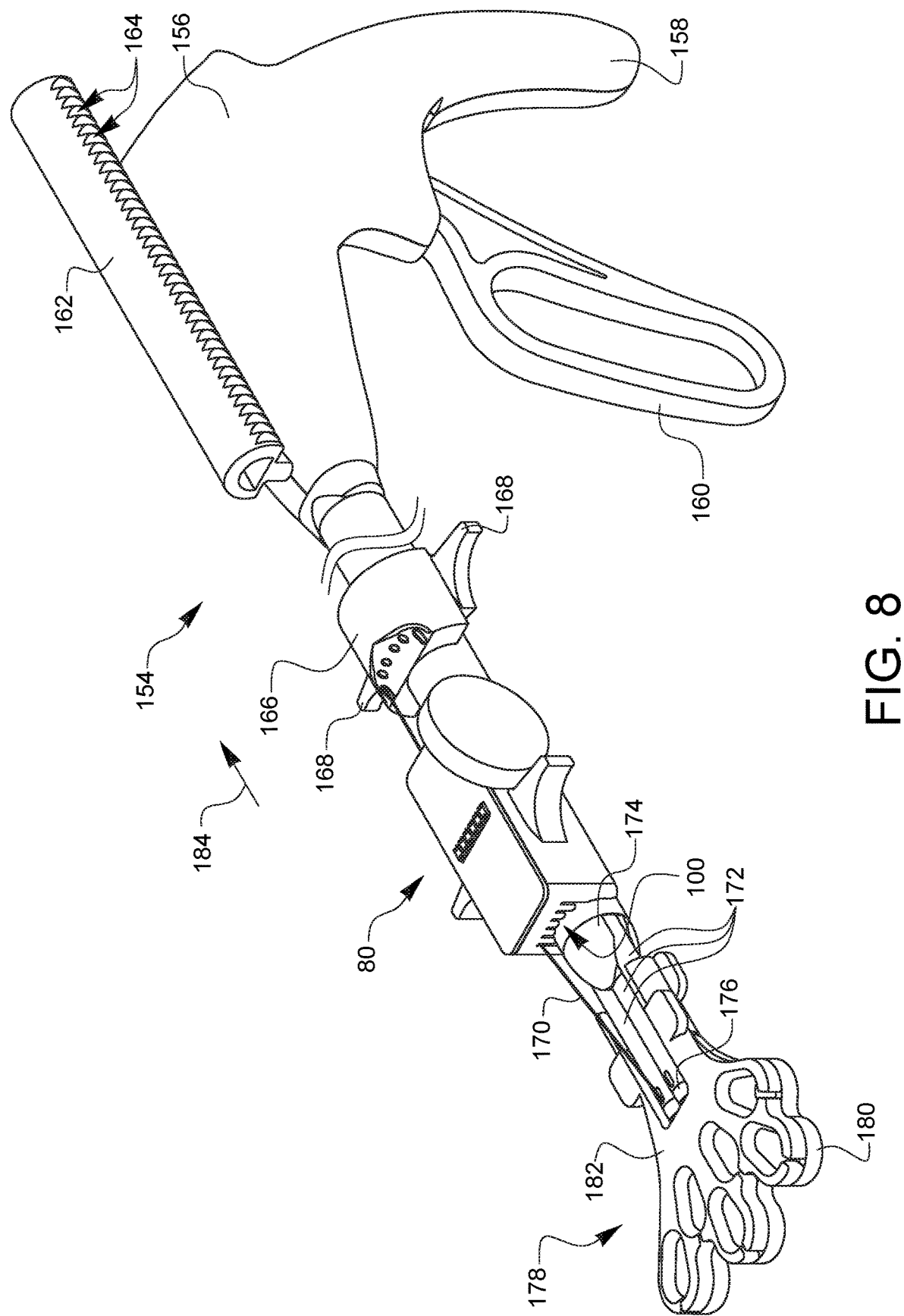
FIG. 8 is a top-left-rear perspective view of another embodiment of a crimping instrument, with the suture tensioning device of FIG. 3A loaded onto the shaft.

FIG. 8 is a top-left-rear perspective view of another embodiment of a crimping instrument, with the suture tensioning device of FIG. 3A loaded onto the shaft. Another embodiment of a crimping instrument 154, having three shafts 172, a shaft support 174, and three crimping ends 176, can fasten three mechanical knots simultaneously. The crimping instrument 154 has a housing 156 defining a handle 158. The instrument 154 has an actuation lever 160 which simultaneously crimps the mechanical fasteners and cuts suture when actuated. The suture tensioning device 80 is placed onto the instrument over the shafts 172. The suture tensioning device 80 is slidably engaged along the shafts 172 by placing the shaft recess 100 over the shafts 172 and can be pulled in a direction towards 184 the operator for the purpose of tensioning suture threaded through one or more mechanical fasteners. On top of the housing 156 there is a guide rail 162 having a plurality of ratchets 164 on either side of the guide rail 162.

The instrument 154 also has a snare assembly or snare loader 178 having a target tray 180 and a target cover 182. A snare 170 within the snare loader 178 is threaded through the suture tensioning device 80 and anchored within the snare puller 166 (the anchoring mechanism is not shown in this view, but may be in the form of a mechanical fastener, handle, snare target or other structure suitable for anchoring a snare to the snare puller 166. The snare puller 166 has ergonomic grips 168 for simultaneously pulling multiple snares in a direction 184 and through the suture tensioning device 80. Similar embodiments such as this may have multiple snares loaded into the snare loader 178 for snaring multiple sutures and threading them through the suture tensioning device 80.

In a minimally invasive surgical procedure requiring multiple sutures that need to be tensioned prior to a mechanical fastening step, the snare 170 pulls the suture through the suture tensioning device 80. Once multiple sutures are threaded through and locked within the suture tensioning device 80, the suture tensioning device 80 may be disengaged from the ends 176 and placed and engaged onto the guide rail 162. If the suture tensioning device 80 needs further tensioning or adjustment in direction 184, the ratchets 164 engage corresponding features in the suture tensioning device 80 to prevent reverse motion relative to direction 184. Other means or methods of retaining the suture tensioning device 80 after tensioning and pulling may be known to those skilled in the art.

Various advantages of an apparatus for suture tensioning have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale.

Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A device for tensioning suture for minimally invasive surgical procedures comprising:
   a housing;
   a first cleat having a first gripping surface, the first cleat being movably connected to the housing;
   a second cleat having a second gripping surface opposing the first gripping surface, the second cleat connected to the housing, and wherein the second cleat and the first cleat are colinear with one another and are arranged along the same linear axis;
   an indicator biasing element connected to the housing; and
   an actuator connected to the housing and in contact with the first cleat;
   wherein the actuator is movable between an unlocked position, a tensioned position, and a locked position, and wherein the device for tensioning suture is configured such that:
      the first cleat is remote from the second cleat, and suture passage through the device for tensioning suture is allowed when the actuator is in the unlocked position;
      the first cleat and the second cleat are in partial contact and suture passage through the device for tensioning suture is partially restricted when the actuator is in the tensioned position;
      the first cleat and the second cleat are in full contact and suture passage through the device for tensioning suture is fully restricted when the actuator is in the locked position,
   wherein the actuator is coupled to the housing when the actuator is in the unlocked position, the tensioned position, and the locked position, and
   wherein the indicator biasing element is configured to provide a visual indication about a tension on the suture and is further configured to be colinear with the first cleat and the second cleat when the suture is under tension.

2. The device for tensioning suture of claim 1, wherein the housing further comprises a suture channel.

3. The device for tensioning suture of claim 1, wherein the housing further comprises a plurality of suture channels.

4. The device for tensioning suture of claim 1, wherein the first cleat further comprises a plurality of recesses.

5. The device for tensioning suture of claim 1, wherein the first cleat further comprises a plurality of flat spots.

6. The device for tensioning suture of claim 1, wherein the second cleat further comprises a plurality of protrusions.

7. The device for tensioning suture of claim 6, wherein the plurality of protrusions are teeth.

8. The device for tensioning suture of claim 7, wherein the teeth are asymmetric.

9. The device for tensioning suture of claim 1, wherein the second cleat further comprises a plurality of recesses.

10. The device for tensioning suture of claim 1, further comprising a cam coupled to the actuator.

11. The device for tensioning suture of claim 1, wherein a holding force on the suture between the first cleat and the second cleat is at least 1 kg.

12. The device for tensioning suture of claim 1, wherein the indicator biasing element further comprises a suture channel.

13. The device for tensioning suture of claim 12, wherein the indicator biasing element is configured such that the indicator biasing element is actuated when:
   a) the actuator is in the locked position; and
   b) the suture held between the first cleat and the second cleat is under tension.

* * * * *